United States Patent [19]

Weinstein

[11] Patent Number: 5,534,995
[45] Date of Patent: Jul. 9, 1996

[54] SCHLIEREN SYSTEM AND METHOD FOR MOVING OBJECTS

[75] Inventor: Leonard M. Weinstein, Newport News, Va.

[73] Assignee: The United States of America as represented by the Administrator of the National Aeronautics and Space Administration, Washington, D.C.

[21] Appl. No.: 388,652

[22] Filed: Feb. 14, 1995

[51] Int. Cl.$^6$ .................................................... G01N 21/45
[52] U.S. Cl. ............................................................... 356/129
[58] Field of Search ................................ 356/129; 73/147

[56] References Cited

U.S. PATENT DOCUMENTS 5,127,264  7/1992  Schmalz .................................... 73/147

*Primary Examiner*—F. L. Evans
*Attorney, Agent, or Firm*—George F. Helfrich

[57] ABSTRACT

A system and method are provided for recording density changes in a flow field surrounding a moving object. A mask having an aperture for regulating the passage of images therethrough is placed in front of an image recording medium. An optical system is placed in front of the mask. A transition having a light field-of-view and a dark field-of-view is located beyond the test object. The optical system focuses an image of the transition at the mask such that the aperture causes a band of light to be defined on the image recording medium. The optical system further focuses an image of the object through the aperture of the mask so that the image of the object appears on the image recording medium. Relative motion is minimized between the mask and the transition. Relative motion is also minimized between the image recording medium and the image of the object. In this way, the image of the object and density changes in a flow field surrounding the object are recorded on the image recording medium when the object crosses the transition in front of the optical system.

19 Claims, 2 Drawing Sheets

SCHLIEREN SYSTEM AND METHOD FOR MOVING OBJECTS

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

1. Field of the Invention

This invention relates to flow field analysis. More specifically, the invention is a schlieren system and method for recording density changes in a flow field surrounding a moving object.

2. Description of the Related Art

Since the early days of flight, scientists have worked to examine the aerodynamic flow field surrounding an aircraft. Typically, scientists are interested in the effects of turbulence and shockwaves on aircraft. However, the invisible nature of air has turned such studies into a branch of research that is carried out with models of the aircraft in wind tunnel environments.

Initially, wind tunnel testing involved injecting streams of smoke into the wind tunnel in order to study the flow around models of aircraft. However, smoke visualization techniques proved inadequate for airplane speeds reaching into the region of compressible flow where shockwaves begin to form. In order to examine compressible flow (as well as any changes in the optical density of any gas or clean liquid), schlieren photographic systems were developed in which shockwaves (or any density changes) appear as dark bands extending from the object or vehicle under examination within a wind tunnel.

A basic schlieren system is shown in the diagrammatic view of FIG. 1 where it is referenced generally by numeral 100. In brief, schlieren system 100 consists of point light source 102 emitting light represented by rays 103, two lenses 104 and 106 on either side of test section 108 of a wind tunnel (not shown) housing model 109, image recording film 110, and mask edge 112 located between lens 106 and film 110 for preventing part of the light passing through lens 106 from impinging on film 110. Specifically, if the air flow in test section 108 is left undisturbed, lens 106 simply reconstructs an image of point source 102 and an image of model 109 for reproduction on film 110. However, if the density of the air moving about model 109 is disturbed, then some of light rays 103 passing around model 109 are bent or refracted. In the example shown, mask edge 112 blocks the light that is bent downward as indicated by dashed line 103a while light that is bent upward continues on. Thus, the ultimate image appearing on film 110 includes an image of model 109 and light and dark bands extending from the image of model 109 to indicate density changes in the air flow about model 109. Such schlieren systems are well known in the art and are disclosed in greater detail by W. Merzkirch, "Flow Visualization", Academic Press, New York, 1974, pages 86–102.

Although producing useful information, wind tunnels are limited since not all flow features of a full scale aircraft in flight can be simulated. On the other hand, in-flight measurements have been limited to using clouds of smoke or tracer particles to either selectively show the outline of an aircraft's features or as a detection medium for velocimeters. Unfortunately, these in-flight techniques require complex, on-board instrumentation and are limited to aircraft flying at moderate speeds, e.g., subsonic speeds of less than 743 miles per hour.

SUMMARY OF THE INVENTION

Accordingly, it is an object of the present invention to provide an apparatus and method for recording density changes in a flow field surrounding a moving object.

Another object of the present invention is to provide an apparatus and method for recording changes in a flow field surrounding an aircraft in flight.

Other objects and advantages of the present invention will become more obvious hereinafter in the specification and drawings.

In accordance with the present invention, a system and method are provided for recording density changes in a flow field surrounding an aerial vehicle in flight. A mask having an aperture for regulating the passage of images therethrough is placed in front of an image recording medium. A telescope is placed in front of the mask. A transition between a light field-of-view and a dark field-of-view is required to be located beyond the aerial vehicle being examined. This transition can be constructed of a composition of components in the sky or a composition of components located at some distance away on the earth's surface. The telescope focuses an image of the transition at the mask such that the aperture causes a band of light to be defined on the image recording medium. The telescope further focuses an image of the aerial vehicle through the aperture of the mask so that the image of the aerial vehicle appears on the image recording medium. Relative motion is minimized between the mask and the transition, and further is minimized between the image recording medium and the image of the aerial vehicle. In this way, the image of the aerial vehicle and density changes in a flow field surrounding the aerial vehicle are recorded on the image recording medium when the aerial vehicle crosses the transition in front of the telescope.

DETAILED DESCRIPTION OF THE INVENTION

Figure 1:
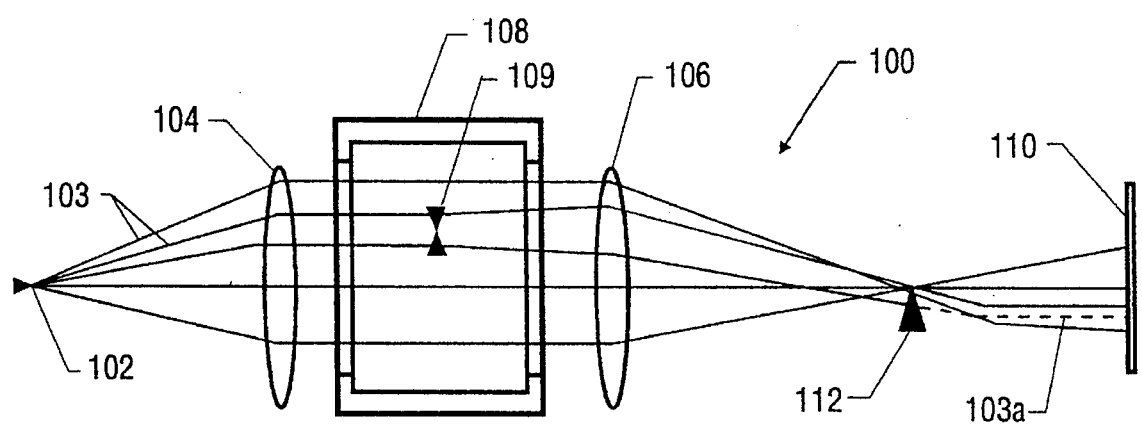
FIG. 1 is a diagrammatic view of a prior art schlieren photographic system.
Figure 2:
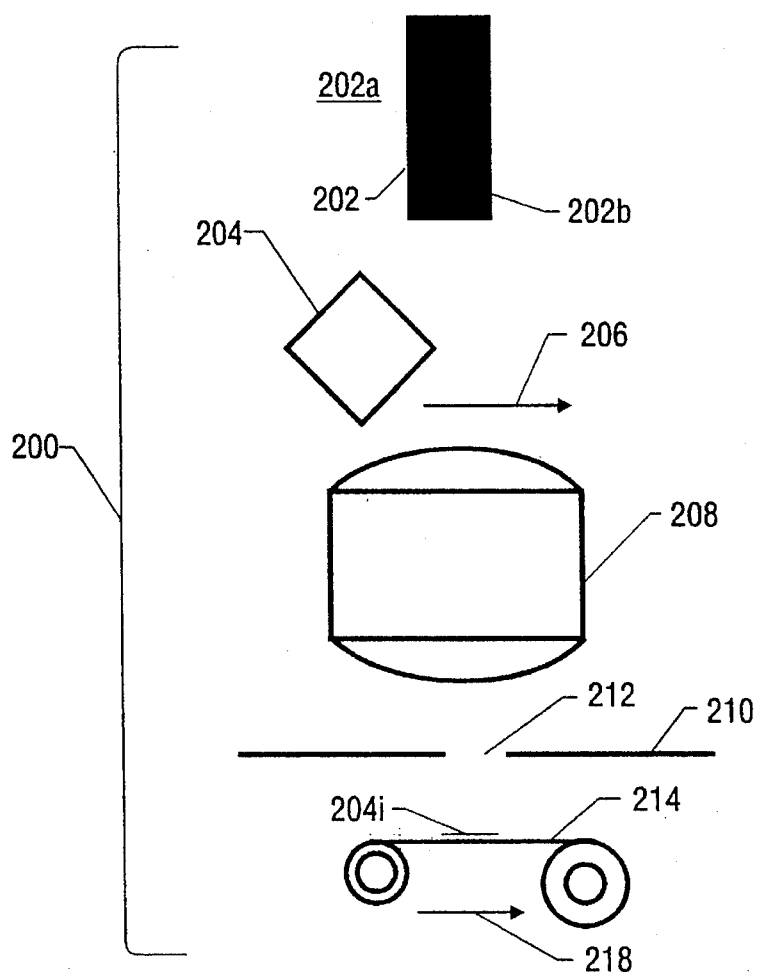
FIG. 2 is a diagrammatic view of a schlieren system according to the present invention used to record density changes in a flow field surrounding a moving object.

Referring now to the drawings, and more particularly to FIG. 2, the method of the present invention will be explained with the aid of a diagrammatic view of schlieren system 200. System 200 includes light-to-dark (or dark-to-light) transition 202, object 204 moving (as referenced by arrow 206) in air or any clear liquid medium along a path that passes between transition 202 and optical system 208, and mask 210 having aperture 212 located between optical system 208 and image recording medium 214.

Transition 202 is any naturally occurring or man-made transition between light field-of-view 202a and dark field of view 202b. In general, the greater the optical difference between light field-of-view 202a and dark field-of-view 202b, the higher the overall sensitivity of system 200. As will become more apparent hereinbelow, depending on the nature of object 204, transition 202 can be established by means of, for example, a dark pole with a white stripe painted thereon, an edge of a building or mountain against a daylight sky, or the edge of a light-emitting celestial body (e.g., sun, moon, etc.) against the sky. The optical gradient between light field-of-view 202a and dark field-of-view 202b is ideally as and must be within constraints to be defined further below.

Object 204 can be any object or vehicle whose movement through air (or clear liquid) is to be studied. Thus, while the present invention will be explained in greater detail below with respect to an aircraft in flight, one of ordinary skill in the art will recognize the potential of utilizing the system and method of the present invention to record density changes in a flow field surrounding any moving object, e.g., person, automobile, train, bullet, etc.

Transition 202 and the path traversed by object 204 are ideally oriented as close to perpendicular as possible for maximum sensitivity to density changes in the flow field surrounding object 204. As the angle between transition 202 and the path traversed by object 204 deviates from 90°, the sensitivity to density changes is reduced in accordance with the law of cosines.

Figure 3:
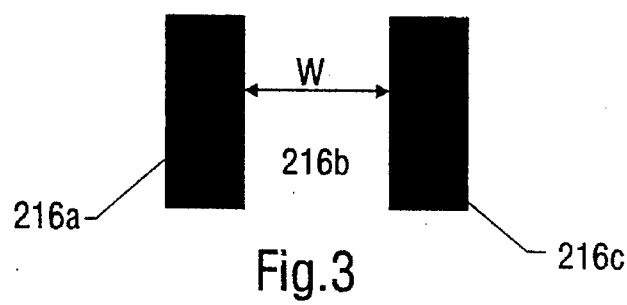
FIG. 3 is a diagrammatic view of the imaged band of light seen by the image recording medium in the schlieren system of the present invention.

Optical system 208 can be any optical system, e.g., telescope, capable of focusing an image of transition 202 at mask 210 while focusing image 204i of object 204 through aperture 212 to image recording medium 214. Aperture 212 is configured to pass a portion of light field-of-view 202a and a portion of dark field-of-view 202b so that image recording medium 214 effectively sees band of light 216b which is shown diagrammatically in FIG. 3. In FIG. 3, imaged band of light 216b is that portion of light field-of-view 202a passed by aperture 212. Band of light 216b is bounded on one side by dark portion 216a which is created by mask 210, and further is bounded on its other side by dark portion 216c which is essentially that portion of dark field-of-view 202b passed by aperture 212. The transition between band of light 216b and dark portion 216c is the image of transition 202. The width W of band of light 216b is defined by the overall sensitivity of system 200. The optical gradient between light field-of-view 202a and dark field-of-view 202b must occur within a distance on the image of transition 202 that is less than W.

To maintain the stability of band of light 216b, it may be necessary to provide an apparatus (not shown in FIG. 2) that minimizes relative motion between transition 202 and mask 210. Factors determining an acceptable amount of relative motion include the choice of transition, the sensitivity of system 200 to changes in width W, etc. The ratio of width W of imaged band of light 216b to the focal length F of optical system 208 defines the sensitivity of system 200. (For example, in the preferred embodiment to be described further below that records density changes in the flow field surrounding an aircraft in flight, a satisfactory W/F ratio was approximately 0.0002 radians. This provided for the detection of refractive angles as small as 4 arc seconds.)

Image recording medium 214 can be any imaging medium, e.g., photographic film, electronic imaging cameras, etc., capable of recording both image 204 and band of light 216b bounded by dark portions 216a and 216c. Regardless of the type of image recording medium used, relative movement should be minimized between image recording medium 214 and image 204,. Typically, this means moving image recording medium 214 to track along with the movement of image 204. Such movement is referenced in FIG. 2 by arrow 218. In this way, as object 204 crosses transition 202, and hence band of light 216b, a schlieren image of the flow field about object 204 is generated at image recording medium 214.

Figure 4:
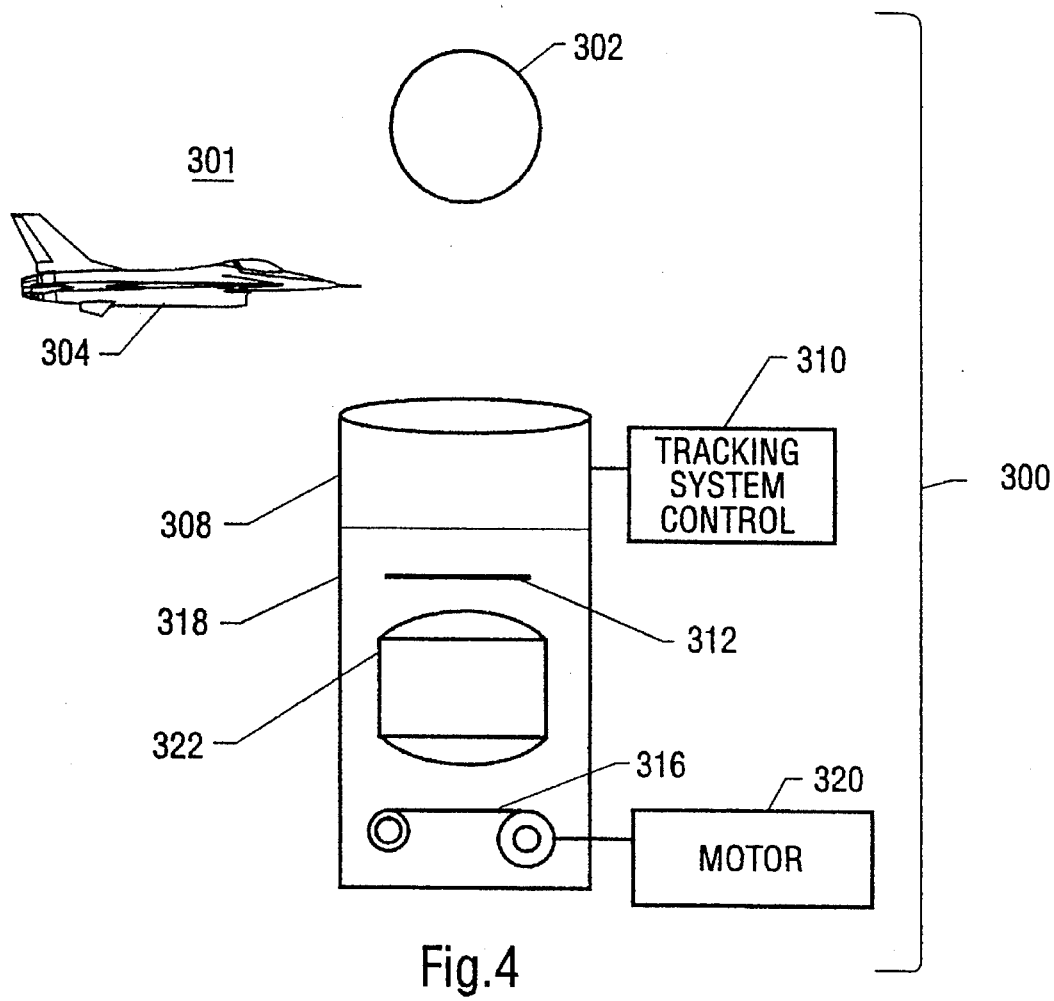
FIG. 4 is a diagrammatic view of a schlieren system according to a preferred embodiment of the present invention configured to record density changes in the flow field surrounding an aircraft in flight.

The present invention is ideally suited for generating schlieren images of an aircraft, e.g., airplane, missile, spacecraft, etc., in flight. A representative set-up for achieving this is shown diagrammatically in FIG. 4 and is referenced generally by numeral 300. The necessary light field-of-view to dark field-of-view is provided by the edge of a light-emitting celestial body, e.g., sun 302 (or the moon), against sky 301. Aircraft 304 is guided along a path to cross substantially perpendicular to the edge of sun 302. Telescope 308 is typically an astronomical telescope equipped with tracking system control 310 for controlling movement of telescope 308 in accordance with movement of sun 302. One example of such a telescope having a tracking system is a model C-8 telescope manufactured by Celestron International, Torrance, Calif., which has a solar rate motor drive to keep the telescope pointed at the sun. Mask 312 having slit 314 (see FIG. 5), and image recording medium 316, are mounted within enclosed housing 318 which is optically coupled to telescope 308. Telescope 308 focuses an image of sun 302 on mask 312 and also focuses an image of aircraft 304 through slit 314. Focusing of telescope 308 can be checked by means of, for example, a video camera (not shown) trained on image recording medium 316.

Figure 5:
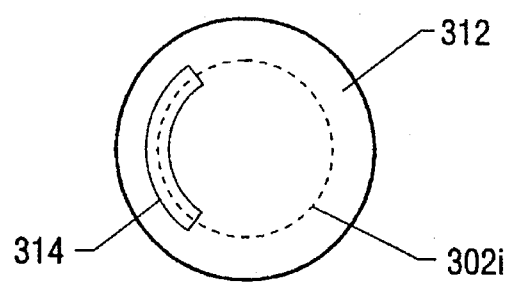
FIG. 5 is a plan view of the mask used to selectively block light from passing to the image recording medium of the present invention schlieren system as well as the image of the sun focused on the mask.

As shown in the plan view of FIG. 5, slit 314 in mask 312 is curved and is aligned such that telescope 308 focuses the edge of image 302 of the sun in slit 314. In this way, the necessary imaged band of light (similar to imaged band of light 216b described above) used by the present invention is created by the combination of the portion of sky 301 passing through slit 314, the edge of image 302i, and the portion of mask 312 blocking the remainder of the sun's image. The length of slit 314 should be sufficient to allow acceptable angular tolerance for the path of aircraft 304.

Image recording medium 316 is, for example, a strip of film moved by motor 320 at a speed that is approximately equal (e.g., within 5–10%) to the speed of the image of aircraft 304 focused by telescope 308 through slit 314. Note that if there is a large distance between telescope 308 and aircraft 304, as is typically the case with any ground mounted telescope, the band of light generated by mask 312 and the image of aircraft 304 (passing through slit 314) may have to be separated. Accordingly, telescope 308 can include relay optical system 322 between mask 312 and image recording medium 316 in order to separate the band of light generated by mask 312 and the image of aircraft 304 passed through slit 314.

The advantages of the present invention are numerous. Flow fields can be examined under "in-flight" conditions. Such information can be used in, for example, studying far-field sonic boom, prototype aircraft development, etc.

Although the invention has been described relative to a specific embodiment thereof, there are numerous variations and modifications that will be readily apparent to those skilled in the art in light of the above teachings. For example, overlapping fields of view could be obtained by providing several of the present invention systems spaced apart in a line at an angle (preferably nearly normal) to the path of the aircraft or other moving object. In this way, a large area of the sky could be covered when an aircraft's path is not accurately known or controllable, or when the flow field of interest is larger than that viewable by a single system. In addition, the present invention could be mounted onboard a movable platform, e.g., chase plane, and moved to the optimum position for recording images. Still further, the moving image recording medium could take the form of a processing and playback imaging system. One such system is an electronic camera operating under "time delay integration" techniques when a moving image is effectively tracked by scanning sequential rows of pixels. In this way, the length of the image is only limited by computer limitations. It is therefore to be understood that, within the scope of the appended claims, the invention may be practiced other than as specifically described.

What is claimed as new and desired to be secured by Letters Patent of the United States is:

1. A system comprising:

an image recording medium;

a mask having an aperture, said mask being placed in front of said image recording medium;

an optical imaging system placed in front of said mask;

an object moving along a path that crosses in front of said optical imaging system;

a transition between a light field-of-view and a dark field-of-view, said transition located such that said object passes between said optical imaging system and said transition;

said optical imaging system focusing an image of said transition at said mask such that said aperture causes a band of light to be defined on said image recording medium, said optical imaging system further focusing an image of said object through said aperture of said mask wherein said image of said object appears on said image recording medium;

means for minimizing relative motion between said mask and said transition; and means for minimizing relative motion between said image recording medium and said image of said object, wherein said image of said object and density changes in a flow field surrounding said object are recorded on said image recording medium when said object crosses said transition.

2. A system as in claim 1 wherein said band of light is substantially perpendicular to said path.

3. A system as in claim 2 wherein said image recording medium is photographic film.

4. A system as in claim 1 wherein said transition occurs naturally in nature.

5. A system as in claim 4 wherein said transition is formed between the sky and the edge of a light-emitting celestial body.

6. A system as in claim 5 wherein said aperture is a slit having a curvature aligned with a curvature of said celestial body.

7. A system as in claim 1 wherein said transition is man-made.

8. A system as in claim 1 further comprising optical means interposed between said image recording medium and said image of said object formed through said aperture, said optical means focusing said image of said of said object focused through said aperture on said image recording medium.

9. A system for recording density changes in a flow field surrounding an aerial vehicle in flight comprising:

an image recording medium;

a mask having an aperture for regulating the passage of images therethrough, said mask being placed in front of said image recording medium;

a telescope placed in front of said mask;

a composition of components defining a transition in the sky between a light field-of-view and a dark field-of-view;

said telescope focusing an image of said transition at said mask such that said aperture causes a band of light to be defined on said image recording medium, said telescope further focusing an image of said aerial vehicle through said aperture of said mask wherein said image of said aerial vehicle appears on said image recording medium;

means for minimizing relative motion between said mask and said transition; and means for minimizing relative motion between said image recording medium and said image of said aerial vehicle, wherein said image of said aerial vehicle and density changes in a flow field surrounding said aerial vehicle are recorded on said image recording medium when said aerial vehicle crosses said transition in front of said telescope.

10. A system as in claim 9 wherein said band of light is substantially perpendicular to said path.

11. A system as in claim 9 wherein said image recording medium is photographic film.

12. A system as in claim 9 wherein said composition of components occur naturally in nature.

13. A system as in claim 12 wherein said composition of components includes the sky and the edge of a light-emitting celestial body.

14. A system as in claim 13 wherein said aperture is a slit having a curvature aligned with a curvature of said celestial body.

15. A system as in claim 9 further comprising optical means interposed between said image recording medium and said image of said aerial vehicle formed through said aperture, said optical means focusing said image of said of said aerial vehicle focused through said aperture on said image recording medium.

16. A method of recording density changes in a flow field surrounding a moving object comprising the steps of:

designating a transition between a light field-of-view and a dark field-of-view;

moving an object along a path that crosses said transition;

providing an image recording medium;

providing a mask having an aperture in front of said image recording medium;

generating an image of said transition at said mask such that said aperture causes a band of light to be defined on said image recording medium;

generating an image of said object such that said image of said object passes through said aperture of said mask wherein said image of said object appears on said image recording medium;

minimizing relative motion between said mask and said transition; and minimizing relative motion between said image recording medium and said image of said object, wherein said image of said object and density changes in a flow field surrounding said object are recorded on said image recording medium when said object crosses said transition.

17. A method according to claim 16 wherein said step of moving said object includes the step of guiding said object so that said path crosses said transition substantially perpendicular thereto.

18. A method according to claim 16 wherein said transition is formed between the sky and the edge of a light-emitting celestial body.

19. A method according to claim 18 wherein said aperture is a curved slit, further comprising the step of aligning said curved slit with a curvature of said celestial body.

* * * * *